US00PP18315P3

(12) United States Plant Patent
Kumar et al.

(10) Patent No.: US PP18,315 P3
(45) Date of Patent: Dec. 18, 2007

(54) **PLANT VARIETY OF *CATHARANTHUS ROSEUS* NAMED 'LLI'**

(50) Latin Name: *Catharanthus roseus*
Varietal Denomination: lli

(75) Inventors: Sushil Kumar, New Delhi (IN); Shashi Pandey Rai, New Delhi (IN); Sanjay Rai Kumar, New Delhi (IN); Digvijay Singh, New Delhi (IN); Suchi Srivastava, New Delhi (IN); Raghvendra Kumar Mishra, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/838,531

(22) Filed: May 4, 2004

(65) Prior Publication Data

US 2005/0251887 P1 Nov. 10, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

| | | | | |
|---|---|---|---|---|
| 6,548,746 B1 | * | 4/2003 | Kulkarni et al. | 800/323 |
| PP15,894 P2 | * | 7/2005 | Brown | Plt./263 |
| 2005/0251887 P1 | * | 11/2005 | Kumar et al. | Plt./263 |

OTHER PUBLICATIONS

Rai, S. et al. Salt–tolerant mutants in glycophytic salinity response (GSR) genes in Catharanthus roeus. Theoretical and Applied Genetics. 106 (2): p. 221–230 published online Sep. 13, 2002, in print Jan. 2003.*

Kulkarni R. et al. Inheritance of morphological traits of periwinkle mutants with modified contents and yields of leaf and root alkaloids. Plant Breeding, 118 (1) p. 71–74 Mar. 1999.*

Bhattacharjee, R. ret al., Mutagenic effectiveness and efficiency of gamma rays ethyl methane sulphonate and nitroso–methyl urea in periwinkle, Catharanthus roseus. Journal of Nuclear Agriculture and Biology. 27 (1) p. 61–64 Mar. 1998.*

Huxley Anthony eds. The New Royal Horticultural Society Dictionary of Gardening The Stock for Press 1992 'Catharanthus' p. 541.*

* cited by examiner

*Primary Examiner*—Wendy Haas
(74) *Attorney, Agent, or Firm*—Ladas and Parry LLP

(57) ABSTRACT

The present invention relates to the development of a unique inflorescence bearing mutant plant type lli/lli (LEAF-LESS INFLORESCENCE). Further the present invention relates to the development of a unique inflorescence bearing mutant plant type lli/lli (LEAF-LESS INFLORESCENCE) through chemical mutagenesis. The present invention relates to the development of a new and distinct plant type for floricultural usage. The new type is a monogenic Mendelian recessive stable mutant plant of *Catharanthus roseus* with a novel leafless inflorescence architecture with increased flower frequency. This distinct plant of *Catharanthus roseus* was developed through chemical mutagenesis followed by salt tolerance selection.

3 Drawing Sheets

Figure 1:
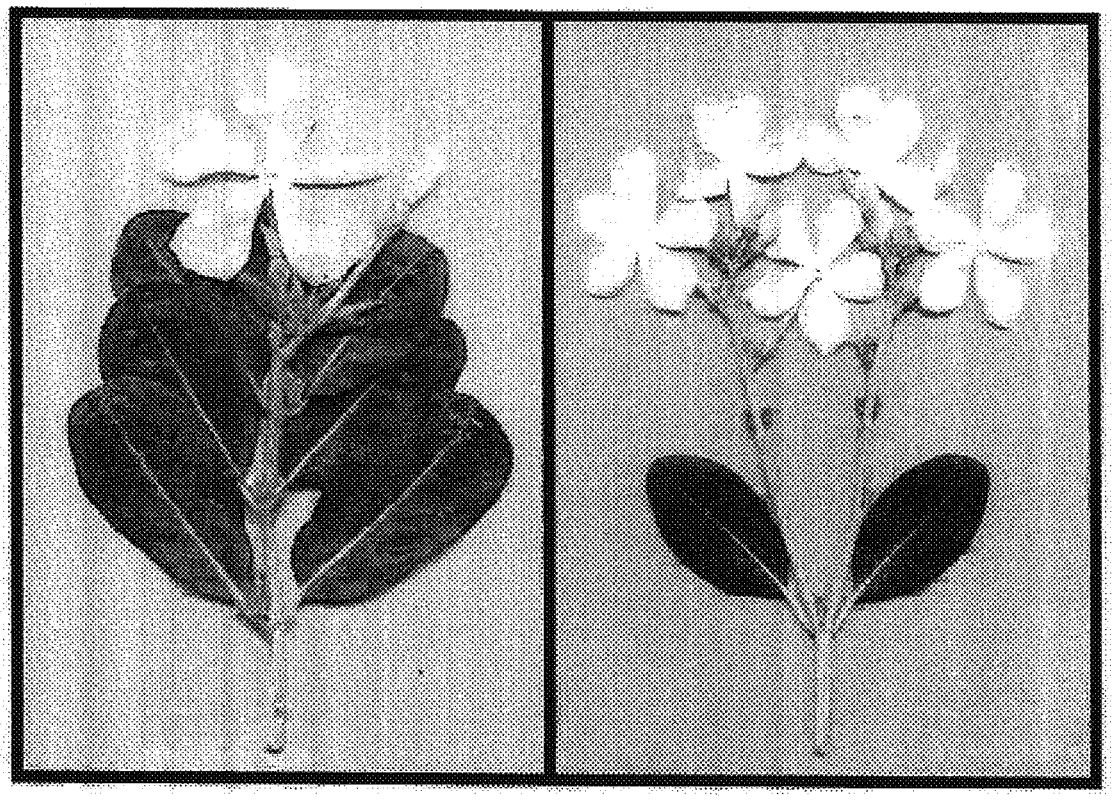

Latin name: *Catharanthus roseus.*
Varietal denomination: lli.

BACKGROUND OF THE INVENTION

Field of Invention

The present invention relates to the development of a unique inflorescence bearing mutant plant type lli/lli (LEAF-LESS INFLORESCENCE). Further the present invention relates to the development of a unique inflorescence bearing mutant plant type lli/lli (LEAF-LESS INFLORESCENCE) through chemical mutagenesis. The present invention relates to the development of a new and distinct plant type for floricultural usage. The new type is a monogenic Mendelian recessive stable mutant plant of *Catharanthus roseus* with a novel leafless inflorescence architecture with increased flower frequency. This distinct plant of *Catharanthus roseus* was developed through chemical mutagenesis followed by salt tolerance selection.

DESCRIPTION OF THE RELATED ART

The Madagascar periwinkle *Catharanthus roseus* (L.) G. Don, a tropical plant of the family Apocynaceae, is a plant that is displayed indoors in all kinds of geographical locations, especially the temperate locations and grown in gardens in semi-temperate to tropical locations on account of its ability to produce flowers all round the year, small size and perenniality.

The species *Catharanthus roseus* enjoys pantropical distribution as its plants grow well under tropical and subtropical environments, It is rarely encountered in temperate environments as low winter temperatures inhibit growth. The characteristic of wide adaptability to all types of soils facilitates its geographically spread distribution in India. Water logged and highly alkaline solis are not suitable for this plant species.

The genus *Catharanthus* is comprised of eight species of small annual or perennial shrubs and herbs, predominantly indigenous to Madagascar: *C. ovalis, C. trichophyllous, C. longifolius, C. coriaceous, C. lanceous* and *C. scitulus.* The species *C. pusillus* has origin in India and *C. roseus* has now naturalized throughout tropics, including tropical and subtropical areas of India. The common features of species in the genus *Catharanthus* include the following: Leaves sessile or short petaloid, entire; Flowers terminal or axillary, solitary or in 2–4 flowers terminated cymes, almost sessile or with very short pedical; Bracts absent; Calyx 5 parted, sepals free almost to the base, narrow, equal without signamellae on the inside; Corolla small to large, salver shaped, rose or white; tube cylindric, slender, externally swollen at the mouth; lobes 5, broad, spreading, overlapping to the left; Stamens 5, attached to the middle of the corolla tube, included Anthers free from stigma and dorsifixed; Pollen ellipsoid, smooth, colporate; Nectary disc represented by two scales, much longer than broad, alternatively with carpels; Carpels 2, distinct, ovules numerous about 10–30 in two series in each carpel; Style long, clavuncle shortly cylindric, truncate at the base; Fruit folliclular, seed numerous non-arrilate, with the hilum in a longitudinal depression on one side, blackish, muriculate, the surface minutely reticulate.

The beauty of this floricultural plant will get furthered if the species is genetically improved to bear higher number of flowers per plant and inflorescence where flowers are borne becomes leafless. *Catharanthus roseus* is also a source of pharmaceutically important terpenoid indole alkaloids (TIAs). Among a spectrum of the secondary metabolites such as alkaloids, anthocyanins, flavonoids, glycosides, saponins, terpenes, essential oils, coumarins and anthraquinones synthesized in many plants, the TIA biosynthesis pathway of *Catharanthus roseus* is of considerable interest on account of its several products that are valuable pharmaceuticals. Whole plant and cell, organ and tissue culture studies have shown that alkaloid biosynthesis in *Catharanthus roseus* responds to stressful conditions. The response of plants to stress apparently is correlated with the hyper-expression of secondary metabolism or pathway(s). The contents of the pharmaceutically important alkaloids in the different organs of *Catharanthus roseus* vary but are low. There is need for developing whole plant and/or single cell genotypes that hyper-synthesize and accumulate anticancerous and/or, cardiotonic TIAs. Hybridization and selection procedures have been used to develop floricultural types in *Catharanthus roseus.* Besides, a variety of approaches have been applied towards the genetic improvement of *Catharanthus roseus* for economic production of its alkaloids. In this regard, the genetic resources from the wild and induced mutants have been examined to identify accessions whose characters can be combined for obtaining desired genotypes. Certain cell cultures and hairy root lines have also been developed in which synthesis of the commercial alkaloids occurs at high levels constitutively or under induced conditions. It appears that genetical investigations on the response to stress may reveal signal pathway(s) shared by the stress responsive genes, and alkaloid biosynthetic pathway genes and/or growth and developmental pathway genes. This approach could be a means to develop improved plant types with better stress response and improved floricultural value and/or higher concentrations of accumulated alkaloids.

SUMMARY OF THE INVENTION

Considerable progress has been made in *Arabidopsis thaliana* and other well worked plant systems such as barley, tomato, tobacco, soybean and maize in the analysis of genes concerned with sensitivity and tolerance to salt stress. In order to be able to use this knowledge and material generated in these heterologous systems, it was considered necessary to develop mutants in *Catharanthus roseus* corresponding to those available in other systems, but with above hypothesis in view. Planned efforts were made to obtain salt tolerant genotype(s) having altered plant architectures. The present invention relates to a salt tolerant mutant with distinct morphology called lli (LEAF-LESS INFLORESCENCE) in 'Nirmal' variety of periwinkle *Catharanthus roseus.* This mutant genotype bears more flowers, and flowers borne on leafless inflorescence stalks and thus offers growers floricultural advantage.

The main objective is to develop a novel variety of *Catharanthus roseus* having distinct morphological features related to salinity tolerance;

Another objective is to develop a novel mutant having hyper-branching associated with improved horticultural/floricultural character in terms of higher levels of flowering.

Yet another objective is to develop a plant type in which flowers are borne on the nodes free of leaves stem stalks that arise from leaf axils.

Still another objective of the invention is to develop unique plant features which can be combined easily with other characters of the *Catharanthus roseus.*

In accordance with these objectives, herein below are described isolation and characteristics of inflorescence and plant architecture in a recessive Mendelian mutant of *Catharanthus roseus.* The main shoot and branches after initial vegetative growth continued to produce branches that bore determinate leafless racemes, while retaining the perennial growth characteristics of the species. The mutant produced more flowers on plant on account of profuse branching. The flowers are produced on nodes on stalks free of leaves. This phenotype is in sharp contrast to the wild type in which the main shoot and branches continue to grow indeterminately producing flowers in the axil of each of the alternate leaves. In comparison to the existing genetic resources, the new mutant displays flowers in larger numbers that are visualized unhindered by leaves.

BRIEF DESCRIPTION OF THE PHOTOGRAPHS

FIG. 1 illustrates on the left side a flowering twig of the wild-type variety 'Nirmal' and illustrates on the right side a flowering twig of the new variety, showing the colors as true as it is reasonably possible to obtain in colored reproductions of this type. Colors in the drawings may differ slightly from the color values cited in the detailed botanical description which accurately describe the colors of the new *Catharanthus;*

Figure 2:
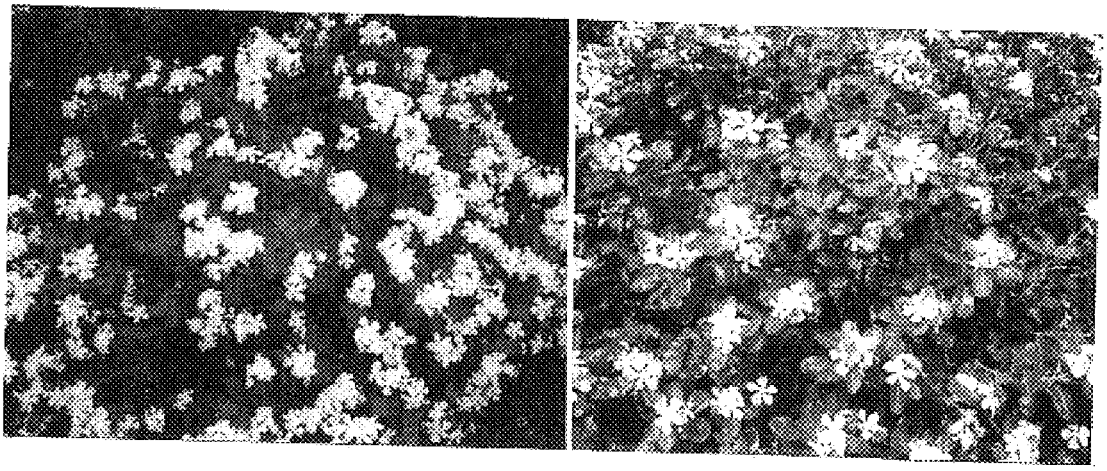
Figure 3:
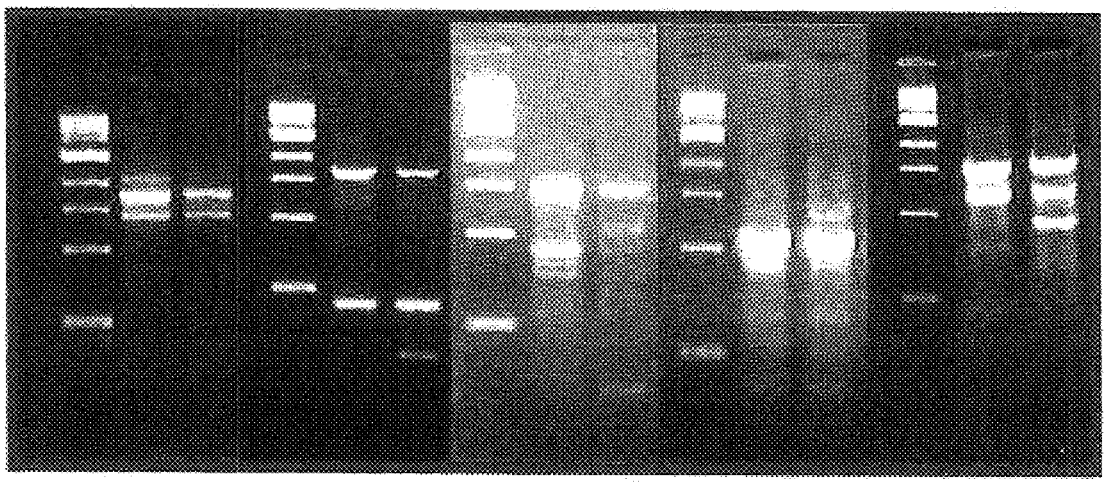

FIG. 2 illustrates on the left side a perspective view of typical flowering plants of 'lli' in plant habitat, and illustrates on the right side a perspective view of typical flowering plants of the wild-type variety 'Nirmal'; and FIG. 3 illustrated RADD profiles of the wild-type and mutant varieties.

BOTANICAL DESCRIPTION OF THE PLANT

The present invention relates to the development of a unique inflorescence bearing mutant plant type lli/lli (LEAF-LESS INFLORESCENCE) through chemical mutagenesis with ethyl methane sulphonate followed by rigorous selection for tolerance to 250 mM NaCl in selfed seed progeny of the familiar fungal resistant variety 'Nirmal' of *Catharanthus roseus*. The mutant lli allele is monogenically recessive to the wild type allele LLI, in Mendelian fashion. The lli mutation is responsible for a pleiotropic phenotype such that the main shoot and branches after initial vegetative growth continue to produce branches bearing functionally determinate leafless inflorescences. Thus in the mutant the number of inflorescence bearing branches is high. One or two flowers are formed on each flowering node. Whole plant-wise, the number of flowers at any time in lli/lli is more than in plant having LLI allele. Leaves being largely absent in the inflorescence of the mutant, the flower display on the plant appears prominent. Because of 75% cross pollination, the mutant characteristics can be maintained by vegetative propagation, or by production of selfed seeds. The vegetative propagation can be by means of cutting, budding, layering and multiple shoot cultures. The lli/lli plants have been maintained vegetatively and by use of selfed seeds for more than 10 cycles. All the morphological plant attributes in lli/lli plants are firmly fixed genetically so as to give a guarantee for pleiotropic morphological characteristics. The pleiotropic characteristic of lli/lli can be combined with any flower colour and plant habit so as to cause improvement in horticultural value.

The invention provides a new and distinct *Catharanthus roseus* plant, developed through mutagenesis possessing the following combination of characters:

a) Said plant type is stable monogenic recessive mutant of *Catharanthus roseus* variety 'Nirmal'.

b) Has distinct inflorescence architecture and plant morphology.

c) Possesses hyper-branching characteristic.

d) Produces higher frequency of flowers.

e) Leaves being largely absent, flowers appear prominent.

f) Mutant plant type can be vegetative propagated by shoot cutting, layering and multiple shoot culture techniques and alternatively by use of selfed seeds.

g) The inflorescence and plant architecture is apparently unique among the inflorescence mutants reported in dicotyledonous plants.

h) The mutant pleiotropic character can be combined with any kind of flower colour and plant habit by cross breeding.

The mutant plant 'lli' can grow on a large variety of soils, including mildly saline soils. Best growth is obtained on sandy loam soil added with farm yard manure/wormicompost. Plant grows well at new Delhi in summer (March to June) and mansoon (July to October) seasons and when temperatures may range from 20° C. to 45° C. However, lower winter temperatures (in December to February) inhibit plant growth. Plant requires periodic irrigation.

The applicant used the seeds of *Catharanthus roseus* cv 'Nirmal' for mutagenesis. About 20,000 seeds were soaked for 8 h in 0.1% (v/v) ethyl methane sulphonate solution in water, then washed in running water for 4 h. The mutagenized seeds were sown in earthen pans filled with 1:1 mixture of soil and farmyard manure. About one month old $M_1$ seedlings were transplanted in the field to obtain $M_2$ seeds. The $M_2$ and control seeds were screened for germination in the presence of high concentrations of NaCl. It had been already shown that control seeds did not germinate in a medium containing more than 150 mM NaCl. To conduct the germination test, the $M_2$ seeds were first surface sterilized using 0.1% $HgCl_2$ (w/v) for one minute, washed thoroughly with sterile distilled water and blotted dry. These were then transferred to petridishes over Whatman no. 1 filter paper circles irrigated with 200 mM NaCl solution, under sterile conditions. The germination test was performed in a culture room at 25±2° C. in a 16 h/8 h light dark cycle. Out of 21,500 $M_2$ seeds, one seedling was found to have germinated in the presence of NaCl. The selected seedling was transplanted over soil and farmyard manure mixture and 6 weeks later to the field. The mutant was observed to have a defective flowering pattern. The $M_3$ selfed seeds were harvested and seeds were tested for resistance to 250 mM NaCl and plants raised from them for the altered inflorescence character to confirm the true breeding behaviour of the mutant. The mutation has now been maintained in pure state in the background of cv. 'Nirmal' for 12 generations. Since the mutant was observed to produce flowers on determinate leafless racemose inflorescences, the wild type allele of the mutant was called as lli for LEAF-LESS INFLORESCENCE and wild type phenotype as LLI for leafy indeterminate racemose inflorescence. The mutant plants appeared to be bushy and short statured because of multibranching character. The comparative growth parameters of the wild type and mutant plants are given in the Table 1, and as follows:

1. Typical and observed ht and diameter of the plant Wild type 63.4±2.3 cm, mutant type 54.3±2.1 The word semi dwarf may be detailed as—Canopy—wild type 20±5 cm, mutant 35±6 cm
2. Typical and observed internode distance Wild type 2.1±0.1 cm, mutant type 1.9±0.2
3. Petiole diameter Wild type 0.4 mm, mutant type 0.4 mm
4. Color of leaf vein Wild type 136D, mutant type 149D
5. Sepal diameter (wild type 0.2±0.1 cm, mutant 0.2±0.1 cm), overall shape (Wild and mutant both-triangular), base shape (wild and mutant Both-flat), margin shape (wild and mutant both-entire), apex shape wild and mutant both-acute); sepal color (Wild type upper 137B, lower 137B, mutant type upper 137B, lower 137C)
6. Flower depth/corolla tube (wild type 2.9±0.1 cm, mutant 2.5±0.1 cm),
7. Upper petal surface coloration-white, lower petal surface coloration-albino white The mutant plants produced more branches, flowers and siliquae and smaller number of leaves than the wild type plants.

Confirmation of mutant stability and inheritance: The stability of pleiotropically changed characters was confirmed by selfing of $M_2$ plants and the mutant has now been maintained in pure state in the background of wild type for more than 10 cycles. To prevent the outcrossing, mutant plants were propagated vegetatively or by use of selfed seeds so that impurity arising from hybridization with other varieties was restricted. The segregation pattern in the $F_2$ generation derived from reciprocal crosses between wild type and mutant genotypes showed that the lli allele was inherited as a Mendalian recessive locus (Table 2). Pleiotropy is defined as changes in a constellation of features resulting from mutation in a gene. The morphology of the mutant lli differed from the wild type *Catharanthus roseus* cv 'Nirmal', pleiotropically. As compared to the wild type the seedlings of the mutant were smaller in size and young leaves had mucronate apex.

TABLE 1

Morphological characteristics of the wild type and lli/lli mutant plants of *Catharanthus roseus* cv Nirmal

| Sl. no. | Characters[a] | Wild type | Mutant 'lli' |
|---|---|---|---|
| 1. | Plant height (cm) | 63.4 ± 2.3 | 54.3 ± 2.1 |
| 2. | Main stem diameter (mm)[b] | 12.0 ± 0.9 | 13.2 ± 0.4 |
| 3. | Internodal length (cm) | 2.1 ± 0.1 | 1.9 ± 0.2 |
| 4. | Number of branches/plant[c] | 27 ± 2 | 45 ± 3 |
| 5. | Number of leaves/plant | 496 ± 18 | 392 ± 21 |
| 6. | Length of petiole | 0.7 ± 0.1 | 0.8 ± 0.1 |
| 7. | Leaf length (cm) | 4.7 ± 0.2 | 3.5 ± 0.2 |
| 8. | Leaf width (cm) | 2.3 ± 0.1 | 2.0 ± 0.1 |
| 9. | Leaf area ($cm^2$)[d] | 8.9 ± 0.1 | 6.4 ± 0.1 |
| 10. | Leaf biomass (g/plant) | 43 ± 2 | 38 ± 2 |
| 11. | Total leaf alkaloids (%) | 1.3 ± 0.6 | 1.9 ± 0.4 |
| 12. | Number of flowers/leaf node | 1.5 ± 0.5 | 10.2 ± 2.1 |
| 13. | Number of flowers/flowering node | 1.5 ± 0.5 | 1.5 ± 0.7 |
| 14. | Number of flowers/plant | 162 ± 25 | 423 ± 45 |
| 15. | Length of corolla tube (cm)[e] | 2.9 ± 0.1 | 2.5 ± 0.1 |
| 16. | Length of petal (cm) | 2.3 ± 0.1 | 2.1 ± 0.1 |
| 17. | Length of sepal (cm) | 0.4 ± 0.2 | 0.3 ± 0.2 |
| 18. | Pollen size (μm) | 62 ± 4 | 60 ± 2 |
| 19. | Pollen fertility (%)[f] | 87 ± 3 | 82 ± 5 |
| 20. | Length of pods (cm) | 2.8 ± 0.1 | 1.5 ± 0.1 |
| 21. | Average number of seeds/siliquae | 16 ± 1 | 12 ± 1 |
| 22. | Weight of 100 seeds (mg) | 81 ± 1 | 80 ± 1 |

[a]all the quantitative observations were taken in 8 months old plants and seeds produced on them;
[b]main stem diameter was measured in the middle of land surface and site of emergence of first branch;
[c]total number of branches were counted;
[d]leaf area was measured by using leaf area meter;
[e]floral morphology was studied by examination of flower under desecting microscope
[f]Spollen fertility was assessed using acetocarmine and fluorochromatic reaction tests (Heslop-Ranson et al., 1970)

TABLE 2

Behaviour of filial generations in crosses involving lli/lli mutant and wild type in *Catharanthus roseus*

| Sl. no. | Crosses and parents[a] | Generation | Number of plants: wild type | Number of plants: mutant type | $X^2$ test[b] |
|---|---|---|---|---|---|
| 1. | Wild type | P | 21[d] | 0 | |
| 2. | Mutant | P | 0 | 12 | |
| 3. | Wild type X mutant | $F_1$ | 32[c] | 0 | |
| 4. | " | $F_2$ | 49 | 18[d] | 0.12 |
| 5. | Mutant X wild type | $F_1$ | 35[c] | 0 | |
| 6. | " | $F_2$ | 35 | 10[d] | 0.18 |

[a]the parents were homozygous mutant and wild type plants;
[b]$x^2$ was calculated on an expected ratio of 3:1; $x^2$ P > 0.05;
[c]the $F_1$ seeds were salt sensitive
[d]the selfed seeds borne on these plants were salt tolerant Multiple shoot cultures are induced from the young apical portions of branches from lli plant. The cultures are initiated, using individual nodes carrying pieces of stem after their sterilization with 0.1% $HgCl_2$ (mercuric chloride) for one minute, on Murashige-Skoog medium supplemented with 3% sucrose solidified with 0.6% agarose with combination of 1 mg/l benzyladenine (BA) and 0.1 mg/l NAA (naphthalene acetic acid). Inoculated tubes are incubated in florescent light of 3000 lux for 16 h/day at ±25° C. After 10 to 15 days of inoculation a number of shoots originate from each node. These new shoots are separated after 4 weeks and sub-cultured for one month in the same medium. When roots have originated from the shoots, the clones are hardened and planted into soil in pots.

In the wild type, the vegetatively growing main shoot and its branches after some growth became indeterminate inflorescence(s), and their apical meristem continued to grow indefinitely. The shoot apical meristem (SAM) in the vegetative phase of the wild type and lli grew to add metamers that comprised of stem, two opposite leaves at a node and in axils of each leaf secondary shoot meristems. Whereas in the wild type, with the onset of reproductive phase the SAM turned into inflorescence apical meristem (IAM) and thereupon produced at each stem node a pair of opposite leaves and in axil of one of them one or two floral meristem(s), the IAM of lli mutant plants grew into a raceme bearing 10–14 flowers, one or two at each node and there were no leaves formed on the raceme nodes. Besides, additional 1 to 2 racemes developed from the axil of one of the last pair of leaves formed by the SAM. The lli plants flowered later in time than wild type plants. Morphology-wise the lli plants appeared to be bushy and short statured as compared to the wild type plants.

The wild type variety 'Nirmal' from which the mutant lli was generated is resistant to the die back disease caused by *Pythium* sp. The lli plants were also die back disease resistant. The lli mutant was found slightly more susceptable to the twig blight caused by *Rhizoctonia solani* than wild type. No major pests, other than oleander hawk moth were seen.

Statement of distinction: The plant of invention (lli/lli) possesses leafless determinate racemose inflorescences to distinguish it from the patent variety 'Nirmal' morphologically. This is shown in FIG. 1. The mutant shows hyper-branching and high frequency of flowers (FIG. 2).

RAPD Analysis: The plant of invention was characterized and compared at DNA level through RAPD analysis. The RAPD profiles of 'Nirmal' and lli/lli were compared with 40 random primers (OPA 1-20, OPB 1-20) procured from Operon Technologies, USA. Out of 40 primers 10 did not respond. The molecular profiles of the plant of invention could be differentiated with 5 primers. (OPA-1, OPA-13, OPB-7, OPB-8 and OPB-17). Thus primers sequence CAGGCCCTTC, CAGCACCCAC, GGTGACGCAG, GTCCACACGG, and AGGGAACGAG allow differentiation of the plant of invention from other varieties (FIG. 3).

PCR conditions: A set of 40 deca-nucleotide primers obtained from Operon Technologies, Inc. (USA) were used for PCR amplification. Polymerase chain reactions (PCR) were carried out in Eppendorf tubes; each reaction mixture contained 25 ng of DNA, 0.2 units of taq DNA polymerase, 100 μM each of the dNTPs, 2 mM $MgCl_2$ and 5 p moles of the primer. The amplification was carried out using DNA Engine 'i cycler (3.021 version)' BioRad. The cycling parameters were the following: cycle 1 (1×) 94° C. for 1 min, 36° C. for 0.30 min., 72° C. for 1 min; cycle 2 (45×) 94° C. for 0.05 min, 36° C. for 0.15 min, 72° C. for 1 min; and cycle 3 (1×) 72° C. for 7 min followed by cycle 4° C. for ∞. The products generated by PCR amplification were separated by electrophoresis in 1.2% agarose gel containing 0.5 g $ml^{-1}$ ethidium bromide. The gel was run with TBE (tris-borate-EDTA buffer) at 60 v for about 4–5 h. In each case 1 Kb λ-DNA ladder digested with EcoRI and Hind III was included to serve as a molecular weight marker and the gel was photographed using Gel Doc System (Alphaimager Tm 2200).

Taxonomic description of the *Catharanthus roseus* mutant plant lli/lli: The description is based upon the observations taken during April month on 180 days old mutant plants growing out doors after planting in Delhi (2001–2003), India with the use of standard agronomic practices. The applicants have referred to the manual as source for the colour code specification for various plant parts, published by Royal Horticultural Society having reference as "Anonymous (2001) R.H.S. Colour Chart, The Royal Horticultural Society, 50 Vincent Square, London SWIP2PE".

1. *Genus.*—*Catharanthus.*
2. *Species.*—*roseus.*
3. *Family.*—Apocynaceae.
4. *Common name.*—Periwinkle.
5. *Plant height.*—Semidwarf.
6. *Growth habit.*—Erect-spreading dwarf.
7. *Stem color.*—Yellow green (144A).
8. *Stem diameter.*—13.2±0.4 mm.
9. *Branch number.*—45–65 (Primary: 15, Secondary: 40–50).
10. *Petiole color.*—Yellow green (124C).
11. *Petiole length.*—Long (0.8±0.1 cm).
12. *Petiole trichomes.*—Present.
13. *Leaf number.*—Medium (392±21).
14. *Leaf shape.*—Obovate.
15. *Leaf apex.*—Mucronate.
16. *Leaf pubescence.*—Very dense (14 on a abaxial and 29 on adaxial surface/unit area).
17. *Leaf size.*—6.4±0.1 $cm^2$.
18. *Leaf angle.*—Nearly right angled.
19. *Leaf venation.*—Reticulate-vein (curved and diverging from mid rib at about 45°).
20. *Leaf colour.*—Upper surface — Yellow green group (YG 144A), lower surface Yellow green group (YG 146B).
21. *Leaf moisture content.*—78%.
22. *Leaf margin.*—Entire.
23. *Leaf base.*—Attenuate.
24. *Stomata type.*—Anisocytic.
25. *Stomatal length.*—28 μm.
26. *Stomatal width.*—14 μm.
27. *Flower inflorescence.*—Determinate terminal racemes.
28. *Flowering node.*—Leaf-less.
29. *Number of flowers/plant.*—350–525.
30. *Sepal colour.*—Yellow green (YG 146B).
31. *Sepal pubescence.*—Dense.
32. *Sepal lobe shape.*—Lanceolate.
33. *Sepal length.*—0.3±0.2 cm.
34. *Petal colour.*—White (W155C).
35. *Petal size.*—3.21 $cm^2$.
36. *Petal length.*—2.1±0.1 cm.
37. *Petal width.*—1.1±0.2 cm.
38. *Petal margin.*—Entire.
39. *Flower diameter.*—40.3±1.1 mm.
40. *Corolla tube length.*—2.5±0.1 cm.
41. *Corolla tube diameter.*—0.3±0.1 cm.
42. *Seed germinability.*—91.7%.
43. *Location of notch on the petal.*—Central.
44. *Stigma.*—Green group (142A). Gynoecium bicarpellary, apocarpous, unilocular; Carpels laterally placed and united by their styles and stigmas; Style long with a disc like stigma at the top forming stigmatic head, the receptive surface of the stigma is situated below.
45. *Style length.*—Short 1.5±0.1 cm.
46. *Anther length.*—2.1±0.2 cm.
47. *Anther width.*—0.3±0.1 cm.
48. *Anthers.*—Stamens five, color yellow (11B), epipetalous, filaments very short, anther sagittate, dorsifixed usually adhered to the stigmatic head by means of a viscid exudate secreted by stigma, pollen granular.
49. *Pollen size.*—60±2 μm.
50. *Pollen shape.*—Elongated.
51. *Pollen fertility.*—82%.
52. *Ovules.*—Light green (142A) few to numerous anatropous.
53. *Ovary.*—0.25 cm, green (143B), superior ovules many, marginal placentation.
54. *Siliqua colour.*—Green group (138A).
55. *Siliqua tip.*—Blunt.
56. *Siliqua orientation.*—Slightly divergent.
57. *Siliqua size.*—1.5 cm, color green (139B).
58. *Siliqua length.*—1.5±0.1 cm.
59. *Siliqua diameter.*—3.1±0.2 mm.
60. *Seed per siliqua.*—12±2.
61. *Seed size.*—2.31±0.12 mm.
62. *Seed shape.*—Oblong.
63. *Seeds.*—Black (202A).
64. *100 seed weight.*—105±1.2 mg.
65. *Seed surface.*—Minutely reticulate.

Plant characteristics: The normal inflorescence in *Catharathus* such as 'Nirmal' is a raceme; two flowers are born at alternate nodes, ad infinitum. In contrast in the mutant the main branch bears terminal flowers and the branch inflorescence bears two flowers/node but the flowering nodes are leafless. Further the growth of leafless raceme is short lived.

Plant propagation: The asexual propagation of mutant as well as wild plant have been done at New Delhi, India using stem cutting and micropropagation using axillary bud explant. The claimed plant has been asexually produced by cutting, layering, budding and multiple shoot culture techniques, beginning in October of 2001 in New Delhi, India and has maintained its characteristics true to type through successive generations of propagations. Further the selfed seeds are obtained by controlled pollination following emasculation.

Brief taxonomical description of family Apocynaceae sps *Catharanthus roseus:* Perrenial herb; leaves opposite; petiolate, inflorescence a raceme; alternate leaves bear two flowers; flowers subsessile, bisexual; corolla sympetalous, stamens carried just below the mouth of tube; anthers almost sessile; 2 carpels; calyx 5 sepals; fruit a pair of narrowly terete many seeded follicles.

Advantages

*Catharanthus roseus* is planted in gardens and kept indoor in pots on account of its characteristic year round bearing of flowers. The plant looks pretty and its varieties bear flowers of different colours, including white. There are many plant species in which flower bearing inflorescence give a view unhindered by leaves, such as in cereals and brassicas. However, in *Catharanthus roseus* natural genetic resources do not demonstrate such character. Therefore it was desired to induce a mutant in *Catharanthus roseus* whose flowers will be displayed prominently unhindered by leaves. Further in *Catharanthus roseus* genetic resources only two flowers are formed per flowering leaf node. In order that the plant will produce more flowers it was desired to induce a mutant which will produce more than two flowers per flowering leaf node and flowers will be visualized unhindered by leaves. Both these goals were achieved by the isolation of lli/lli mutant in *Catharanthus roseus.* As a result of the present work the lli/lli plants of *Catharanthus roseus* of 4 months or more age produce 25 to 400% more flowers displayed prominently as compared to the parental varieties. The lli/lli *Catharanthus roseus* represent significant advance in the floricultural value of the species.

Floricultural advantages

The lli/lli mutant plants of *Catharanthus roseus* retain constant flower bearing, short stature and perenniality characteristics of the species. They bear several to many flowers on stalks that arise from the axils of leaves at the top of branches, unlike in the existing genetic resources where one or two flowers are produced in the axils of leaves. The mutant plants bear more branches and therefore 25 to 400% more flowers than the existing genetic resources in plants of ages varying from 4 to 18 month. The canopy of the mutant is spreading in nature while being erect in habit like the parent variety. The lli/lli plants are relatively more tolerant to salt/drought than the parental variety(ies). Therefore, lli/lli mutants of *Catharanthus roseus* represent genetically improved plant type with several floricultural features absent in the existing genetic resources.

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial
<220> FEATURE:
<223> OTHER INFORMATION: Primer for differentiating the mutant plant
      type lli/lli from others

<400> SEQUENCE: 1

caggcccttc                                                          10


<210> SEQ ID NO 2
<211> LENGTH: 10
<212> TYPE: DNA
<213> ORGANISM: Artificial
<220> FEATURE:
<223> OTHER INFORMATION: Primer for differentiating the mutant plant
      type lli/lli from others

<400> SEQUENCE: 2

cagcacccac                                                          10


<210> SEQ ID NO 3
<211> LENGTH: 10
<212> TYPE: DNA
<213> ORGANISM: Artificial
<220> FEATURE:
<223> OTHER INFORMATION: Primer for differentiating the mutant plant
      type lli/lli from others

<400> SEQUENCE: 3

ggtgacgcag                                                          10


<210> SEQ ID NO 4
<211> LENGTH: 10
<212> TYPE: DNA
<213> ORGANISM: Artificial
<220> FEATURE:
<223> OTHER INFORMATION: Primer for differentiating the mutant plant
      type lli/lli from others

<400> SEQUENCE: 4

gtccacacgg                                                          10


<210> SEQ ID NO 5
<211> LENGTH: 10
<212> TYPE: DNA
<213> ORGANISM: Artificial
<220> FEATURE:
<223> OTHER INFORMATION: Primer for differentiating the mutant plant
      type lli/lli from others
```

-continued

```
<400> SEQUENCE: 5

agggaacgag                                                          10
```

We claim:

1. A new and distinct variety of *Catharanthus roseus* plant, as herein illustrated and described.

* * * * *